US012797132B2

(12) United States Patent
Zhang et al.

(10) Patent No.: US 12,797,132 B2
(45) Date of Patent: Nov. 17, 2026

(54) IMAGE REGISTRATION METHOD AND SYSTEM FOR NAVIGATION IN FEMORAL NECK FRACTURE SURGERY

(71) Applicants: THE FIRST MEDICAL CENTER OF PLA GENERAL HOSPITAL, Beijing (CN); BEIJING AKSO MEDICAL TECHNOLOGY DEVELOPMENT CO., LTD, Beijing (CN)

(72) Inventors: Lihai Zhang, Beijing (CN); Yang Luo, Beijing (CN); Yong Liu, Beijing (CN); Dezheng Song, Beijing (CN); Liang Li, Beijing (CN); Nian Zheng, Beijing (CN); Ye Peng, Beijing (CN); Gongzi Zhang, Beijing (CN); Shuwei Zhang, Beijing (CN); Bin Shi, Beijing (CN)

(73) Assignees: THE FIRST MEDICAL CENTER OF PLA GENERAL HOSPITAL, Beijing (CN); BEIJING AKSO MEDICAL TECHNOLOGY DEVELOPMENT CO., LTD, Beijing (CN)

( * ) Notice: Subject to any disclaimer, the term of this patent is extended or adjusted under 35 U.S.C. 154(b) by 325 days.

(21) Appl. No.: 18/575,710

(22) PCT Filed: Nov. 9, 2022

(86) PCT No.: PCT/CN2022/130810

§ 371 (c)(1),
(2) Date: Dec. 29, 2023

(87) PCT Pub. No.: WO2023/240912

PCT Pub. Date: Dec. 21, 2023

(65) Prior Publication Data

US 2024/0315776 A1 Sep. 26, 2024

(30) Foreign Application Priority Data

Jun. 14, 2022 (CN) ......................... 202210684949.2

(51) Int. Cl.
*A61B 5/00* (2006.01)
*A61B 6/00* (2006.01)
(Continued)

(52) U.S. Cl.
CPC .............. *A61B 34/10* (2016.02); *A61B 6/032* (2013.01); *A61B 6/466* (2013.01); *A61B 6/505* (2013.01);
(Continued)

(58) Field of Classification Search
CPC ......... A61B 34/10; A61B 34/20; A61B 6/032; A61B 6/505; A61B 6/5217;
(Continued)

(56) References Cited

U.S. PATENT DOCUMENTS

2006/0291710 A1* 12/2006 Wang ...................... G06T 15/08 382/154
2007/0127845 A1 6/2007 Fu et al.
2013/0211232 A1 8/2013 Murphy et al.

FOREIGN PATENT DOCUMENTS

CN 104637061 A 5/2015
CN 109925057 A 6/2019
(Continued)

OTHER PUBLICATIONS

Lei, Y., et al., "An Improved 2D-3D Medical Image Registration Algorithm based on Modified Mutual Information and Expanded Powell Method," 2013 ISSS International Conference on Medical Imaging Physics and Engineering, Jul. 26, 2014.
(Continued)

*Primary Examiner* — Joel F Brutus
(74) *Attorney, Agent, or Firm* — Cozen O'Connor

(57) ABSTRACT

The present disclosure provides an image registration method and system for navigation in femoral neck fracture surgery, an electronic device, and a computer-readable storage medium. The method includes: obtaining femoral image data by a computed tomography (CT) imaging device before surgery and obtaining a surgical path planned by a doctor to generate a three-dimensional femoral image with the surgical path; obtaining, during the surgery, X-ray images photographed by an X-ray machine at different angles, and extracting feature points on each of the X-ray images; setting digitally reconstructured radiograph (DRR) virtual scene projection parameters based on a structure of the X-ray machine, projecting the three-dimensional femoral image with the surgical path to generate a plurality of DRR images, and extracting feature points on each of the DRR
(Continued)

images; and automatically registering the DRR image and the X-ray image, and outputting a surgical path after registration.

10 Claims, 8 Drawing Sheets

(51) Int. Cl.

| | |
|---|---|
| ***A61B 6/03*** | (2006.01) |
| ***A61B 6/46*** | (2024.01) |
| ***A61B 6/50*** | (2024.01) |
| ***A61B 34/10*** | (2016.01) |
| ***A61B 34/20*** | (2016.01) |

(52) U.S. Cl.
CPC ............ *A61B 6/5217* (2013.01); *A61B 34/20* (2016.02); *A61B 2034/105* (2016.02); *A61B 2034/107* (2016.02); *A61B 2034/108* (2016.02)

(58) Field of Classification Search
CPC ........ A61B 2034/105; A61B 2034/107; A61B 2034/108
See application file for complete search history.

(56) References Cited

FOREIGN PATENT DOCUMENTS

| | | | |
|---|---|---|---|
| CN | 112184782 | A | 1/2021 |
| CN | 112509022 | A | 3/2021 |
| CN | 112825619 | A | 5/2021 |
| CN | 115068110 | A | 9/2022 |
| JP | 2020054794 | A | 4/2020 |

OTHER PUBLICATIONS

International Search Report for PCT/CN2022/130810, mailed Mar. 8, 2023, 8 pages (with English translation).

* cited by examiner

IMAGE REGISTRATION METHOD AND SYSTEM FOR NAVIGATION IN FEMORAL NECK FRACTURE SURGERY

CROSS REFERENCE TO RELATED APPLICATION

The present application is a national stage application of International Patent Application No. PCT/CN2022/130810, filed on Nov. 9, 2022, which claims priority to the Chinese Patent Application No. 202210684949.2, filed with the China National Intellectual Property Administration (CNIPA) on Jun. 14, 2022, and entitled "IMAGE REGISTRATION METHOD AND SYSTEM FOR NAVIGATION IN FEMORAL NECK FRACTURE SURGERY", which is incorporated herein by reference in its entirety.

TECHNICAL FIELD

The present disclosure relates to the technical field of medical image registration for orthopedic surgical navigation, and in particular, to an image registration method and system for navigation in femoral neck fracture surgery.

BACKGROUND

Computer-aided surgical navigation is a system technology that has developed rapidly in the past decade. Based on medical images, with the assistance of high-performance computers and professional software, the computer-aided surgical navigation realizes accurate minimally invasive surgery by tracking and positioning surgical instruments, which greatly improves a success rate of surgery and reduces surgical complications.

Currently, the orthopedic treatment is usually to collect computed tomography (CT) volume data of a diseased region before operation, design a surgical plan based on a visual reconstruction model, and collect X-ray images during the operation to provide real-time information to adjust the surgical plan. Intraoperative two-dimensional X-ray images lack three-dimensional spatial information, so that doctors can only determine by means of their own experience and spatial imagination, and thus it is necessary to register a preoperative three-dimensional CT model with the intraoperative X-ray images to provide more comprehensive and accurate information. The objective of the registration is to obtain a positional relationship between a three-dimensional structure and the two-dimensional X-ray images in a surgical environment. A usual method is to project three-dimensional data onto a two-dimensional plane, transform the problem into registration between two pieces of two-dimensional data, and constantly adjust projection parameters, so as to realize registration between the two-dimensional data and three-dimensional volume data.

A femur is a tubular bone that has a complex structure, bears the highest load, and is the most valuable for human behavior. Femoral neck needs to undertake movement and support functions of most human activities, and a therapeutic effect against its fracture will directly affect the quality of life of patients after illness. Currently, femoral neck fracture accounts for 3.6% of all fractures in the elderly with osteoporosis, and its incidence is increasing year by year as the aging of society is intensified. However, image registration methods special for navigation in femoral neck fracture surgery were rarely reported. Therefore, it is an urgent need to provide an image registration method featuring simple operations, high speed and high precision, which can be applied to navigation in femoral neck fracture surgery.

SUMMARY

An objective of the present disclosure is to provide an image registration method and system for navigation in femoral neck fracture surgery, which can be applied to navigation in femoral neck fracture surgery, and features simpleness in operation, high speed and high precision.

To achieve the above objective, the present disclosure provides the following solutions:

An image registration method for navigation in femoral neck fracture surgery includes:

- obtaining femoral image data by a computed tomography (CT) imaging device before femoral neck fracture surgery;
- reconstructing and segmenting the femoral image data to generate a three-dimensional femoral image;
- obtaining a surgical path planned by a doctor on the three-dimensional femoral image to generate a three-dimensional femoral image with the surgical path;
- obtaining, during the femoral neck fracture surgery, X-ray images photographed by an X-ray machine at different angles, where the different angles include an anteroposterior/posteroanterior view and a lateral view;
- performing data processing on each of the X-ray images, and extracting feature points of the X-ray image;
- setting digitally reconstructured radiograph (DRR) virtual scene projection parameters based on a structure of the X-ray machine, projecting the three-dimensional femoral image with the surgical path to generate a plurality of DRR images, and obtaining projection pose coordinates and a surgical path of each of the DRR images;
- performing data processing on the DRR image, and extracting feature points of the DRR image; and
- automatically registering the DRR image and the X-ray image based on a similarity between the feature points of the X-ray image and the feature points of the DRR image, and outputting a surgical path after registration.

Optionally, the performing data processing on each of the X-ray images, and extracting feature points of the X-ray image specifically includes:

- obtaining regional feature points selected in a femoral head region of the X-ray image; generating a femoral head fitting circle with the regional feature points; generating a series of contour circles based on the femoral head fitting circle; identifying a femoral outer contour of the X-ray image based on a femoral outer contour line segment template; and extracting intersection points of the series of contour circles and the femoral outer contour as the feature points of the X-ray image.

Optionally, the setting DRR virtual scene projection parameters based on a structure of the X-ray machine, projecting the three-dimensional femoral image with the surgical path to generate a plurality of DRR images specifically includes:

- setting the DRR virtual scene projection parameters based on the structure of the X-ray machine, and expressing a pose parameter corresponding to the three-dimensional femoral image as $P=(\theta x, \theta y, \theta z, Px, Py, Pz)$, where $\theta x$, $\theta y$ and $\theta z$ represent rotation angles of a femur around three principal axes, X, Y and Z, in a projection reference coordinate system, respectively; Px, Py and Pz represent translation amounts of the femur in directions of the three principal axes, X, Y and Z, in the projection reference coordinate system, respectively; and projecting the three-dimensional femoral image with the surgical path along the three principal axes at intervals of a preset translation length and a preset rotation angle to generate the plurality of DRR images.

Optionally, the performing data processing on each of the DRR images, and extracting feature points of the DRR image specifically includes:

performing data processing on the DRR image to generate a femoral outer contour and a series of contour circles of a femoral head of the DRR image; and extracting intersection points of the series of contour circles and the femoral outer contour as the feature points of the DRR image.

Optionally, the automatically registering the DRR image and the X-ray image based on a similarity between the feature points of the X-ray image and the feature points of the DRR image, and outputting a surgical path after registration specifically includes:

comparing the similarity between the feature points of the X-ray image with the feature points of the DRR image, and if an anteroposterior/posteroanterior image and a lateral image successfully match within an error range, obtaining a surgical path of a successfully matched DRR image; and outputting the surgical path after registration based on the surgical path of the successfully matched DRR image.

An image registration system for navigation in femoral neck fracture surgery includes:

a femoral image data acquisition module, configured to obtain femoral image data by a CT imaging device before femoral neck fracture surgery;

a three-dimensional femoral image reconstruction module, configured to reconstruct and segment the femoral image data to generate a three-dimensional femoral image;

a surgical path planning module, configured to obtain a surgical path planned by a doctor on the three-dimensional femoral image to generate a three-dimensional femoral image with the surgical path;

an X-ray image acquisition module, configured to obtain, during the femoral neck fracture surgery, X-ray images photographed by an X-ray machine at different angles, where the different angles include an anteroposterior/posteroanterior view and a lateral view;

an X-ray image feature point extraction module, configured to perform data processing on each of the X-ray images, and extract feature points of the X-ray image;

a DRR image generation module, configured to set DRR virtual scene projection parameters based on a structure of the X-ray machine, project the three-dimensional femoral image with the surgical path to generate a plurality of DRR images, and obtain projection pose coordinates and a surgical path of each of the DRR images;

a DRR image feature point extraction module, configured to perform data processing on the DRR image, and extract feature points of the DRR image; and an image registration module, configured to automatically register the DRR image and the X-ray image based on a similarity between the feature points of the X-ray image and the feature points of the DRR image, and output a surgical path after registration.

Optionally, the X-ray image feature point extraction module specifically includes:

a regional feature point selection unit, configured to obtain regional feature points selected in a femoral head region of the X-ray image; a femoral head fitting circle generating unit, configured to generate a femoral head fitting circle with the regional feature points; a unit for generating a series of contour circles, configured to generate a series of contour circles based on the femoral head fitting circle; a femoral outer contour identification unit, configured to identify a femoral outer contour of the X-ray image based on a femoral outer contour line segment template; and an X-ray image feature point extraction unit, configured to extract intersection points of the series of contour circles and the femoral outer contour as the feature points of the X-ray image.

Optionally, the DRR image generation module specifically includes:

a DRR virtual scene projection parameter setting unit, configured to set the DRR virtual scene projection parameters based on the structure of the X-ray machine, and express a pose parameter corresponding to the three-dimensional femoral image as P=(θx, θy, θz, Px, Py, Pz), where Ox, Oy and θz represent rotation angles of a femur around three principal axes, X, Y and Z, in a projection reference coordinate system, respectively; Px, Py and Pz represent translation amounts of the femur in directions of the three principal axes, X, Y and Z, in the projection reference coordinate system, respectively; and a DRR image generating unit, configured to project the three-dimensional femoral image with the surgical path along the three principal axes at intervals of a preset translation length and a preset rotation angle to generate the plurality of DRR images.

Optionally, the DRR image feature point extraction module specifically includes:

a unit for generating a femoral outer contour and a series of contour circles, configured to perform data processing on the DRR image to generate a femoral outer contour and a series of contour circles of a femoral head of the DRR image; and a DRR image feature point extraction unit, configured to extract intersection points of the series of contour circles and the femoral outer contour as the feature points of the DRR image.

Optionally, the image registration module specifically includes:

an image registration unit, configured to compare the similarity between the feature points of the X-ray image with the feature points of the DRR image, and if an anteroposterior/posteroanterior image and a lateral image successfully match within an error range, obtain a surgical path of a successfully matched DRR image; and a unit for outputting a surgical path after registration, configured to output the surgical path after registration based on the surgical path of the successfully matched DRR image.

An electronic device includes one or more processors and one or more memories configured to store one or more programs, where when the one or more programs are executed by the one or more processors, the one or more processors are enabled to implement the image registration method for navigation in femoral neck fracture surgery.

A computer-readable storage medium in which computer instructions are stored is provided, where when the computer instructions are executed, the computer-readable storage medium is enabled to implement the image registration method for navigation in femoral neck fracture surgery.

According to specific embodiments of the present disclosure, the present disclosure has the following technical effects:

The present disclosure provides an image registration method and system for navigation in femoral neck fracture surgery, an electronic device, and a computer-readable storage medium. The method includes: obtaining femoral image data by a CT imaging device before femoral neck fracture surgery; reconstructing and segmenting the femoral image data to generate a three-dimensional femoral image; obtaining a surgical path planned by a doctor on the three-dimensional femoral image to generate a three-dimensional femoral image with the surgical path; obtaining, during the femoral neck fracture surgery, X-ray images photographed by an X-ray machine at different angles, where the different angles include an anteroposterior/posteroanterior view and a lateral view; performing data processing on each of the X-ray images, and extracting feature points of the X-ray image; setting DRR virtual scene projection parameters based on a structure of the X-ray machine, projecting the three-dimensional femoral image with the surgical path to generate a plurality of DRR images, and obtaining projection pose coordinates and a surgical path of each of the DRR images; performing data processing on the DRR image, and extracting feature points of the DRR image; and automatically registering the DRR image and the X-ray image based on a similarity between the feature points of the X-ray image and the feature points of the DRR image, and outputting a surgical path after registration. The method and system according to the present disclosure can be applied to navigation in femoral neck fracture surgery, and features simpleness in operation, high speed and high precision.

BRIEF DESCRIPTION OF THE DRAWINGS

To describe the technical solutions in embodiments of the present disclosure or in the prior art more clearly, the accompanying drawings required for the embodiments are briefly described below. Apparently, the accompanying drawings in the following description show merely some embodiments of the present disclosure, and those of ordinary skill in the art may still derive other accompanying drawings from these accompanying drawings without creative efforts.

DETAILED DESCRIPTION OF THE EMBODIMENTS

The technical solutions of embodiments of the present disclosure are clearly and completely described below with reference to the accompanying drawings in the embodiments of the present disclosure. Apparently, the described embodiments are merely some rather than all of the embodiments of the present disclosure. All other embodiments obtained by those of ordinary skill in the art based on the embodiments of the present disclosure without creative efforts shall fall within the protection scope of the present disclosure.

An objective of the present disclosure is to provide an image registration method and system for navigation in femoral neck fracture surgery, which can be applied to navigation in femoral neck fracture surgery, and features simpleness in operation, high speed and high precision.

In order to make the above objective, features and advantages of the present disclosure clearer and more comprehensible, the present disclosure will be further described in detail below in combination with accompanying drawings and specific implementations.

Based on registration conditions, medical image registration mainly falls into two categories: registration based on external information and registration based on internal information of images.

The registration based on external information is based on an external marker attached to a bone tissue. A method of registration using an external marker has the advantages of high registration accuracy and low time consumption. However, this method needs to implant the marker before surgery, which may cause additional harm to a patient. In addition, the deviation of the marker before and during the surgery may introduce errors.

The registration based on internal information of images is to obtain image features from preoperative image data and find corresponding features in corresponding intraoperative images, so as to realize spatial transformation between preoperative images and intraoperative images. Internal information of an image includes internal features of the image and an intensity of the image. Internal features of an image may be further classified as feature points, feature curves, and feature surfaces. Intensity-based image registration uses intensity information of pixels for registration.

According to the present disclosure, the feature-based registration method is applied to the process of registration of a preoperative three-dimensional image and an intraoperative two-dimensional image of a femur, which is simple to operate, convenient and intuitive.

Figure 1:
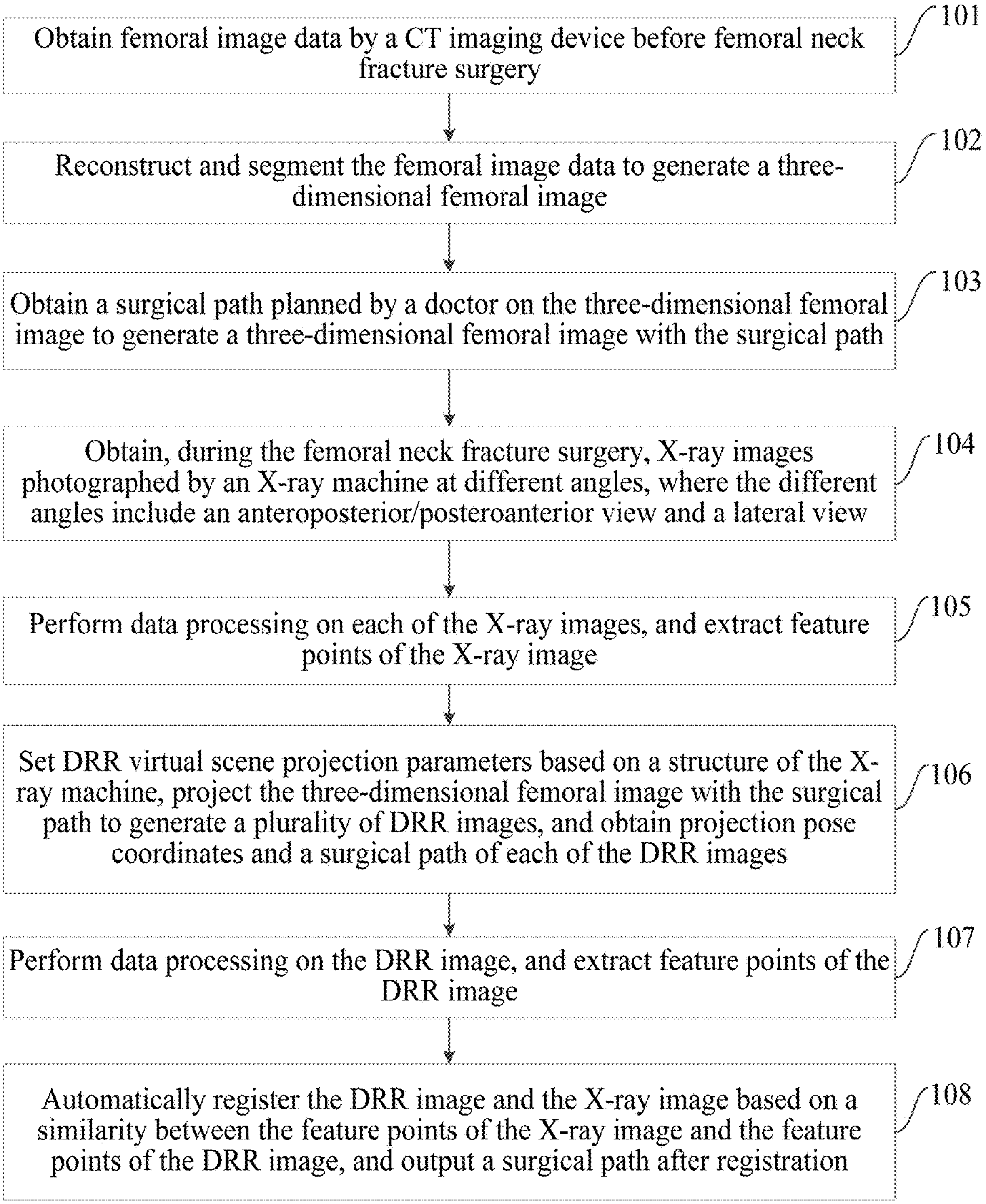
FIG. 1 is a flowchart of an image registration method for navigation in femoral neck fracture surgery according to the present disclosure.
Figure 2:
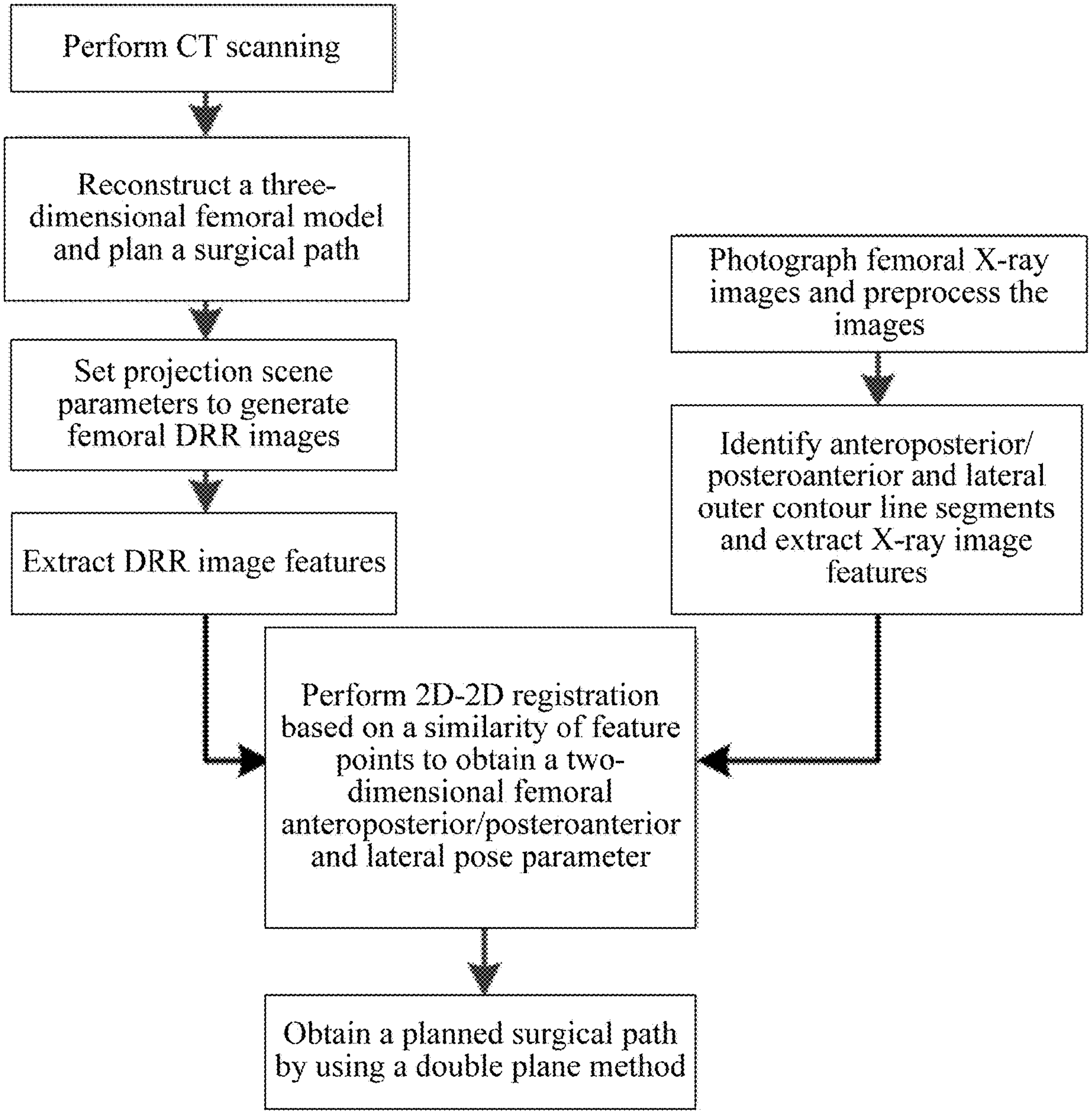
FIG. 2 is a schematic diagram of a principle of an image registration method for navigation in femoral neck fracture surgery according to the present disclosure.

FIG. 1 is a flowchart of an image registration method for navigation in femoral neck fracture surgery according to the present disclosure, and FIG. 2 is a schematic diagram of a principle of an image registration method for navigation in femoral neck fracture surgery according to the present disclosure. Referring to FIGS. 1 and 2, an image registration method for navigation in femoral neck fracture surgery according to the present disclosure includes the following steps.

Step 101: Obtain femoral image data by a CT imaging device before femoral neck fracture surgery.

According to the present disclosure, before the surgery, the femoral image data is obtained by the CT imaging device, and the like, so that the femoral image data can be reconstructed and segmented to generate a three-dimensional femoral image.

Step 102: Reconstruct and segment the femoral image data to generate a three-dimensional femoral image.

Femoral CT three-dimensional reconstruction and segmentation are performed based on the femoral image data to generate three-dimensional femoral data, that is, to generate a three-dimensional femoral image.

Step 103: Obtain a surgical path planned by a doctor on the three-dimensional femoral image to generate a three-dimensional femoral image with the surgical path.

The doctor plans the surgical path, fits a three-dimensional femoral head into a sphere, and determines the radius of the sphere.

Step 104: Obtain, during the femoral neck fracture surgery, X-ray images photographed by an X-ray machine at different angles, where the different angles include an anteroposterior/posteroanterior view and a lateral view.

During the surgery, two-dimensional X-ray images (referred to as X-ray images or X-ray films) including the anteroposterior/posteroanterior view and the lateral view and photographed by the X-ray machine such as a C-arm at different angles are obtained, and at least two X-ray films of a femur at different angles are taken. In practical application, preferably, three two-dimensional X-ray images are obtained, which facilitates multiple registration constraints and can help to determine a result.

Step 105: Perform data processing on each of the X-ray images, and extract feature points of the X-ray image.

Usually, the doctor manually selects a plurality of regional feature points from femoral head regions of anteroposterior/posteroanterior and lateral X-ray films. A computer performs data processing on the X-ray images to obtain the regional feature points to generate a fitting circle, two sections of femoral outer contour lines of the X-ray films are identified and determined based on a template of outer contour lines from greater trochanter to a femoral shaft and from lesser trochanter to the femoral shaft, and intersection points of a series of contour circles generated by the femoral head fitting circle and the two sections of outer contour lines are used as feature point of registration.

In practical application, at least three regional feature points are selected from the position of the femoral head in the X-ray film to generate a femoral head fitting circle. The template of outer contour lines from the greater trochanter to the femoral shaft and from the lesser trochanter to the femoral shaft is based on femoral outer contour lines obtained from anteroposterior/posteroanterior and lateral X-ray films vertically and horizontally photographed by the X-ray machine when a human body is lying horizontally, and its size is statistically significant. The contour lines are automatically obtained when the two sections of outer contours are placed near anteroposterior/posteroanterior and lateral outer contours of the X-ray film during registration.

Therefore, step 105 of performing data processing on each of the X-ray images, and extracting feature points of the X-ray image specifically includes:

obtaining regional feature points selected in a femoral head region of the X-ray image; generating a femoral head fitting circle with the regional feature points; generating a series of contour circles based on the femoral head fitting circle; identifying a femoral outer contour of the X-ray image based on a femoral outer contour line segment template; and extracting intersection points of the series of contour circles and the femoral outer contour as the feature points of the X-ray image.

Step 106: Set DRR virtual scene projection parameters based on a structure of the X-ray machine, project the three-dimensional femoral image with the surgical path to generate a plurality of DRR images, and obtain projection pose coordinates and a surgical path of each of the DRR images.

Initial DRR projection scene parameters are set based on the structure of the X-ray machine and surgical requirements, and a pose parameter corresponding to the three-dimensional femoral image is P=(θx, θy, θz, Px, Py, Pz), where θx, θy and θz represent rotation angles of the femur around three principal axes in a projection reference coordinate system; Px, Py and Pz represent translation amounts of the femur in directions of the three principal axes in the projection reference coordinate system; and the plurality of DRR images (also referred to as two-dimensional DRR images) are generated along the three principal axes at intervals of a preset translation length and rotation angle. To generate the plurality of DRR images of the femur, it is needed to set a translation range and a rotation range, where a preset length of a minimum translation interval is 1-2 mm, and a preset angle of a minimum rotation interval is 1-2°.

In practical application, a relative position relationship between light sources and screens is determined based on the structure of the X-ray machine, and a virtual X-ray projection and photographing system is established to simulate a scene of the X-ray machine taking femoral anteroposterior/posteroanterior and lateral films. Two cameras at right angles to each other are used to simulate emission sources of the X-ray machine, and two screens at right angles to each other are used to simulate X-ray screens. One camera corresponds to one screen. It is ensured that the camera is opposite to the screen, and a spatial distance between the camera and the screen is equal to a distance between an actual emission source of the X-ray machine and the screen.

Three-dimensional femoral data (namely the three-dimensional femoral images with a surgical path) is imported into the virtual X-ray photographing system, and the radius of a three-dimensional fitting ball head and the radius of a femoral head fitting circle in anteroposterior/posteroanterior and lateral films are compared to determine a distance between the femoral head and a point light source and a distance between the femoral head and an imaging plane. The position of the three-dimensional fitting ball head in a projection section is determined based on the position of the femoral head fitting circle in the X-ray film. In DRR, initial positions of the femoral head are Px0, Py0, and Pz0.

Principal component analysis (PCA) is used to determine a principal axis direction of the three-dimensional femoral contour and a principal axis direction of the femoral contour in the X-ray film, and the initial directions of the two principal axes are the same during DRR projection. In DRR, initial poses of the femoral head are θx0, θy0, and θz0.

Therefore, step 106 of setting DRR virtual scene projection parameters based on a structure of the X-ray machine, projecting the three-dimensional femoral image with the surgical path to generate a plurality of DRR images specifically includes:

setting the DRR virtual scene projection parameters based on the structure of the X-ray machine, and expressing a pose parameter corresponding to the three-dimensional femoral image as P=(θx, θy, θz, Px, Py, Pz), where θx, θy and θz represent rotation angles of the femur around three principal axes, X, Y and Z, in a projection reference coordinate system, respectively; Px, Py and Pz represent translation amounts of the femur in directions of the three principal axes, X, Y and Z, in the projection reference coordinate system, respectively; and projecting the three-dimensional femoral image with the surgical path along the three principal axes at intervals of a preset translation length (usually 1-2 mm) and a preset rotation angle (usually 1-2°) to generate the plurality of DRR images.

Step 107: Perform data processing on the DRR image, and extract feature points of the DRR image.

Data processing is performed on each DRR image to automatically generate a femoral outer contour line, and automatically generate a series of feature circles and intersection points of the series of feature circles and the femoral outer contour as feature points of registration.

Therefore, step 107 of performing data processing on the DRR image, and extracting feature points of the DRR image specifically includes:

performing data processing on the DRR image to generate a femoral outer contour and a series of contour circles of a femoral head of the DRR image; and extracting intersection points of the series of contour circles and the femoral outer contour as the feature points of the DRR image.

Step 108: Automatically register the DRR image and the X-ray image based on a similarity between the feature points of the X-ray image and the feature points of the DRR image, and output a surgical path after registration.

Each DRR image is automatically registered with the X-ray image, a reference coordinate system of the DRR image coincides with a reference coordinate system of the X-ray image, the similarity between the feature points are compared, and if an anteroposterior/posteroanterior image and a lateral image successfully match within an error range, surgical path information of a successfully matched two-dimensional DRR image is obtained. Two-dimensional X-ray images that are not registered during the surgery are used as anteroposterior/posteroanterior and lateral auxiliary images to display the surgical path after registration in real time.

The planned surgical path of the DRR image after accurate registration is output, and the registration of the preoperative three-dimensional image and the intraoperative two-dimensional image is completed.

Therefore, step 108 of automatically registering the DRR image and the X-ray image based on a similarity between the feature points of the X-ray image and the feature points of the DRR image, and outputting a surgical path after registration specifically includes:

comparing the similarity between the feature points of the X-ray image with the feature points of the DRR image, and if an anteroposterior/posteroanterior image and a lateral image successfully match within an error range, obtaining a surgical path of a successfully matched DRR image; and outputting the surgical path after registration based on the surgical path of the successfully matched DRR image.

In an image registration method for navigation in femoral neck fracture surgery according to the present disclosure, before surgery, CT images of a patient's femur and other photographed data are processed to generate three-dimensional volume data (three-dimensional femoral image), and a surgical path planned by a doctor is obtained; during the surgery, two-dimensional X-ray images photographed by an X-ray machine at different angles are obtained; feature points are selected from a femoral head region of an X-ray film to generate a fitting circle, a femoral outer contour of the X-ray film is identified based on a femoral outer contour line segment template, and a series of feature circles and feature points are automatically generated; DRR virtual scene projection parameters are set based on a structure of the X-ray machine, a plurality of two-dimensional DRR images similar to X-ray films are generated by projecting the three-dimensional femoral volume data, and projection pose coordinates and a surgical path of each image are obtained; the DRR image data is processed to automatically extract an outer contour, and automatically generate feature circles and feature points; and a surgical path after accurate registration is output based on a similarity of feature points of the DRR images and the X-ray films as the basis for determining accurate registration of the preoperative three-dimensional image and the intraoperative two-dimensional X-ray images. The method according to the present disclosure improves accuracy of registration of the preoperative three-dimensional image and the intraoperative two-dimensional images of the femur, is simple to operate, visual and reliable, and has good surgical effects and few complications.

A specific embodiment of the method of the present disclosure applied to image registration for orthopedic surgical navigation is provided below with reference to the accompanying drawings.

The method embodiment specifically included the following steps.

Figure 3:
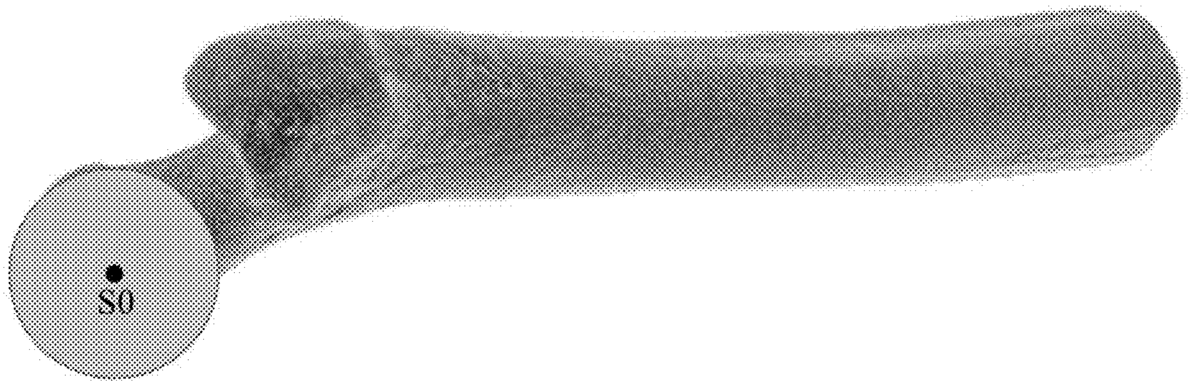
FIG. 3 is a schematic diagram showing femoral CT three-dimensional reconstruction according to an embodiment of the present disclosure.

1): Before surgery, femoral image data was obtained by a CT imaging device, and a three-dimensional femoral image was generated by reconstruction and segmentation, as shown in FIG. 3; a surgical path planned by a doctor was obtained; a three-dimensional femoral head was fitted to be spherical, with a center of the sphere being S0, and a radius of the sphere was determined.

2): During the surgery, two-dimensional X-ray images including an anteroposterior/posteroanterior view and a lateral view and photographed by an X-ray machine such as a C-arm at different angles were obtained, and an included angle during photographing of the anteroposterior/posteroanterior view and the lateral view was 90°.

Figure 4:
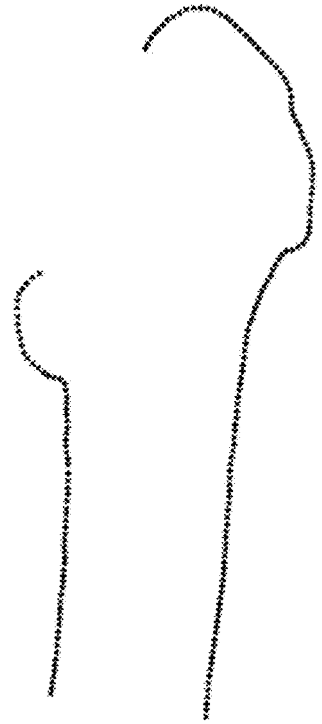
FIG. 4 is a schematic diagram of a femoral outer contour line segment template according to an embodiment of the present disclosure.
Figure 5:
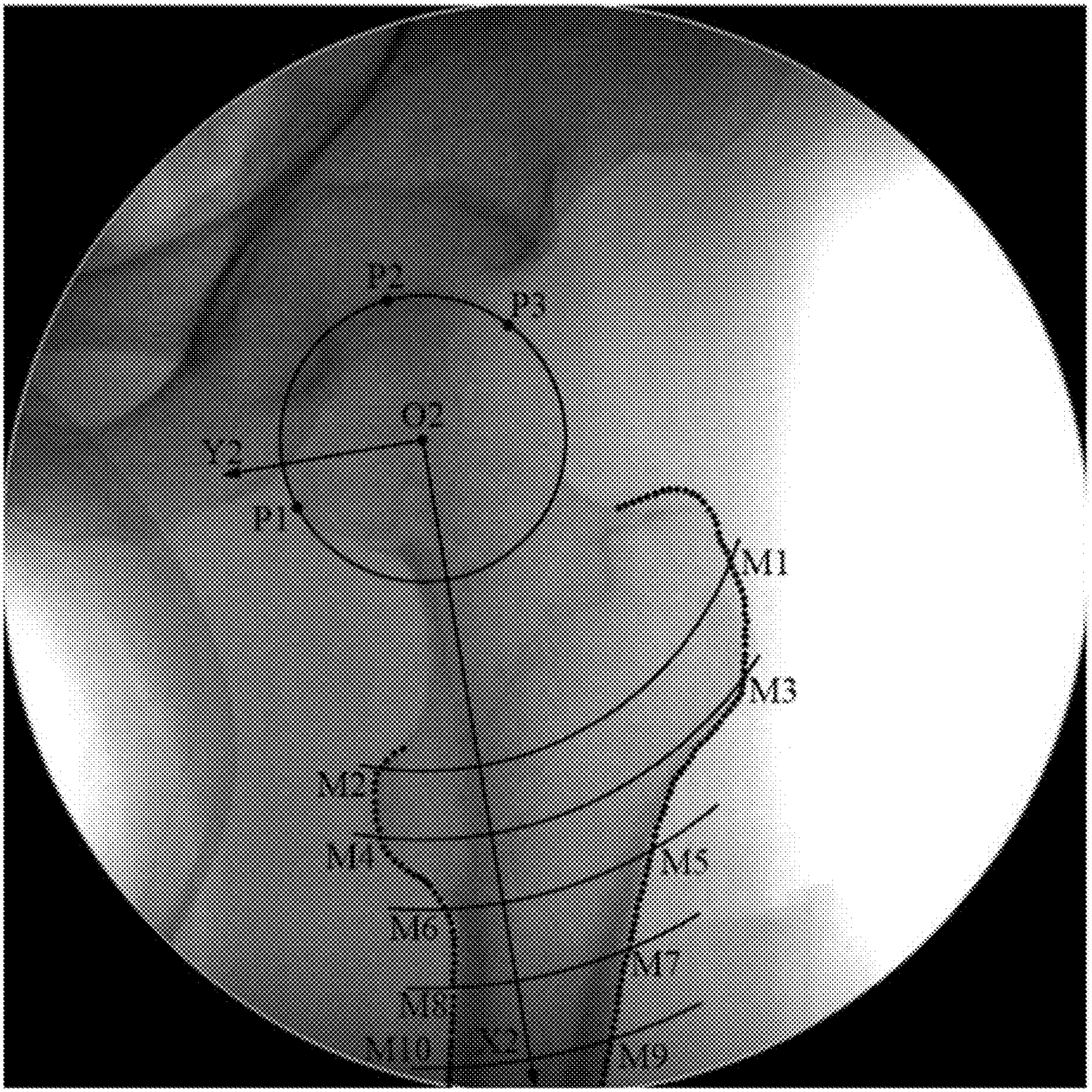
FIG. 5 is a schematic diagram showing extraction of contour feature points of an X-ray femoral image according to an embodiment of the present disclosure.

3): Anteroposterior/posteroanterior and lateral X-ray films were processed. Taking the anteroposterior/posteroanterior view as an example, as shown in FIG. 5, regional feature points P1, P2 and P3 were manually selected from a femoral head region of the anteroposterior/posteroanterior X-ray film to generate a fitting circle O2, two sections of femoral outer contour lines of the X-ray film were identified and determined based on a template of outer contour lines from greater trochanter to a femoral shaft and from lesser trochanter to the femoral shaft (as shown in FIG. 4), a series of contour circles were generated based on the femoral head fitting circle O2, and intersection points of the series of contour circles and the two sections of outer contour lines were M1, M2, M3, M4, M5, M6, M7, M8, M9, and M10 as feature points of X-ray film registration. X2 was a midpoint of an M9M10 line segment, and a Y2O2 axis was perpendicular to an O2X2 axis.

Figure 6:
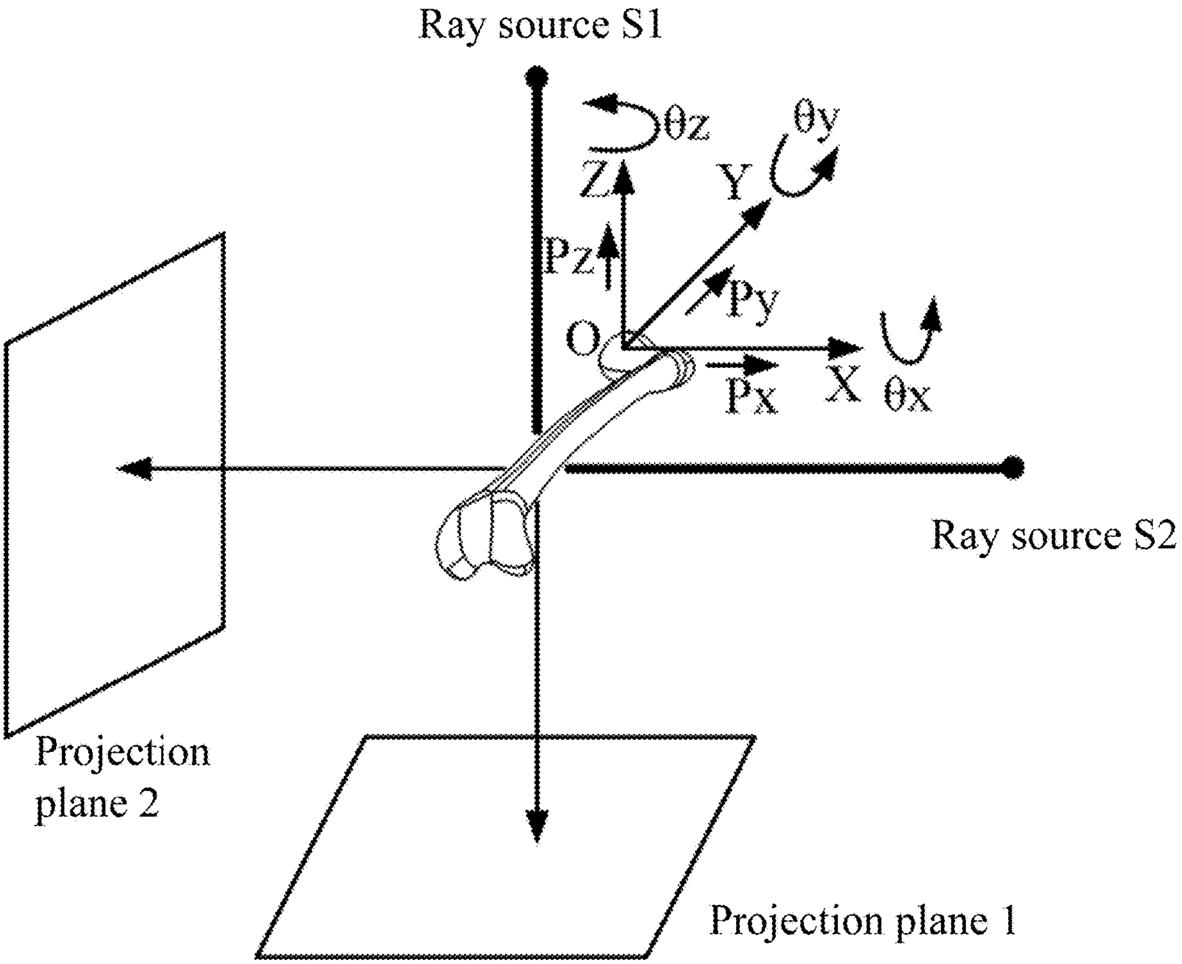
FIG. 6 is a schematic diagram showing femoral DRR projection according to an embodiment of the present disclosure.

4): Initial DRR projection scene parameters were set based on the structure of the X-ray machine and surgical requirements. As shown in FIG. 6, ray sources S1 and S2 and projection planes 1 and 2 were set, a positional relationship between the ray sources and the projection planes was consistent with that of the X-ray machine, and a pose parameter corresponding to the three-dimensional femoral image was P=(θx, θy, θz, Px, Py, Pz), where θx, θy and θz represented rotation angles of a femur around three principal axes in a projection reference coordinate system OXYZ; Px, Py and Pz represent translation amounts of the femur in directions of the three principal axes in the projection reference coordinate system OXYZ; and a plurality of DRR images were generated along the three principal axes at intervals of a preset translation length of 2 mm and a preset rotation angle of 2°.

Figure 7:
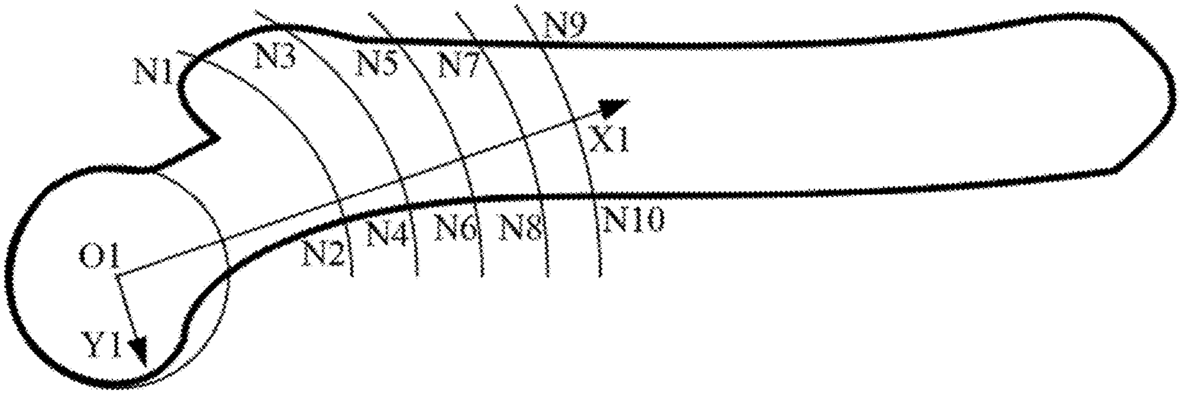
FIG. 7 is a schematic diagram showing automatic extraction of contour feature points from a femoral DRR image according to an embodiment of the present disclosure.

5): Data processing was performed on each DRR image. As shown in FIG. 7, a femoral outer contour line was automatically generated, a series of femoral head feature circles were automatically generated, with a circle center being 01, and intersection points of the feature circles and the femoral outer contour were N1, N2, N3, N4, N5, N6, N7, N8, N9 and N10 as feature points of DRR image registration. X1 was a midpoint of an N9N10 line segment, and a Y1O1 axis is perpendicular to an O1X1 axis.

6): Each DRR image was automatically registered with the X-ray image, a reference coordinate system O1X1Y1Z1 of the DRR image coincided with a reference coordinate system O2X2Y2Z2 of the X-ray image, the similarity between the feature points N1-N10 and M1-M10 were compared, and if an anteroposterior/posteroanterior image and a lateral image successfully matched within an error range, surgical path information of a two-dimensional DRR image was obtained.

7): The planned surgical path of the DRR image after accurate registration was output, and the registration of the preoperative three-dimensional image and the intraoperative two-dimensional image was completed by using a double plane method.

Figure 8:
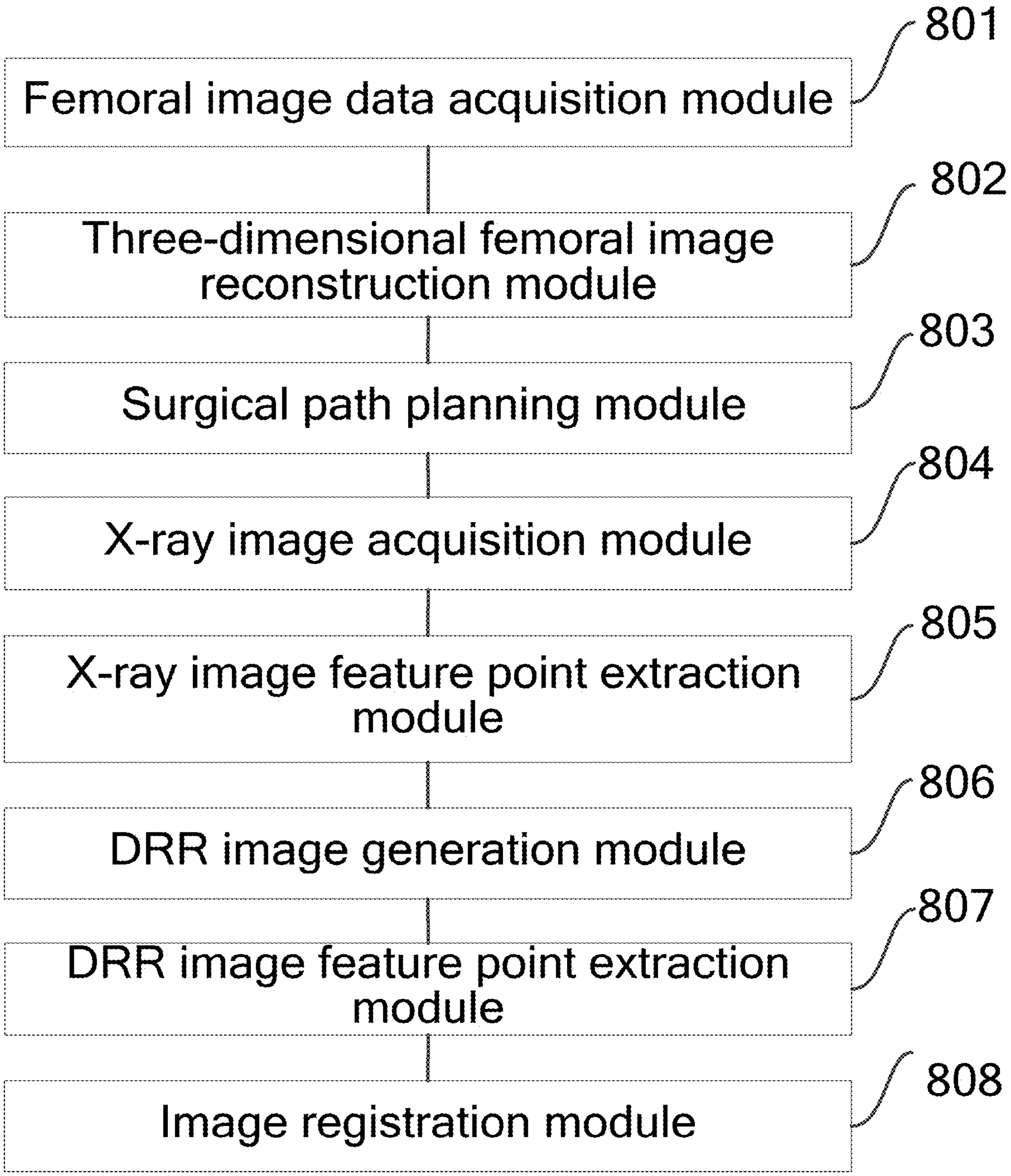
FIG. 8 is a structural diagram of an image registration system for navigation in femoral neck fracture surgery according to the present disclosure.

Based on the image registration method for navigation in femoral neck fracture surgery according to the present disclosure, the present disclosure further provides an image registration system for navigation in femoral neck fracture surgery. Referring to FIG. 8, the system includes:

a femoral image data acquisition module 801, configured to obtain femoral image data by a CT imaging device before femoral neck fracture surgery;

a three-dimensional femoral image reconstruction module 802, configured to reconstruct and segment the femoral image data to generate a three-dimensional femoral image;

a surgical path planning module 803, configured to obtain a surgical path planned by a doctor on the three-dimensional femoral image to generate a three-dimensional femoral image with the surgical path;

an X-ray image acquisition module 804, configured to obtain, during the femoral neck fracture surgery, X-ray images photographed by an X-ray machine at different angles, where the different angles include an anteroposterior/posteroanterior view and a lateral view;

an X-ray image feature point extraction module 805, configured to perform data processing on each of the X-ray images, and extract feature points of the X-ray image;

a DRR image generation module 806, configured to set DRR virtual scene projection parameters based on a structure of the X-ray machine, project the three-dimensional femoral image with the surgical path to generate a plurality of DRR images, and obtain projection pose coordinates and a surgical path of each of the DRR images;

a DRR image feature point extraction module 807, configured to perform data processing on the DRR image, and extract feature points of the DRR image; and an image registration module 808, configured to automatically register the DRR image and the X-ray image based on a similarity between the feature points of the X-ray image and the feature points of the DRR image, and output a surgical path after registration.

The X-ray image feature point extraction module 805 specifically includes:

a regional feature point selection unit, configured to obtain regional feature points selected in a femoral head region of the X-ray image; a femoral head fitting circle generating unit, configured to generate a femoral head fitting circle with the regional feature points; a unit for generating a series of contour circles, configured to generate a series of contour circles based on the femoral head fitting circle; a femoral outer contour identification unit, configured to identify a femoral outer contour of the X-ray image based on a femoral outer contour line segment template; and an X-ray image feature point extraction unit, configured to extract intersection points of the series of contour circles and the femoral outer contour as the feature points of the X-ray image.

The DRR image generation module 806 specifically includes:

a DRR virtual scene projection parameter setting unit, configured to set the DRR virtual scene projection parameters based on the structure of the X-ray machine, and express a pose parameter corresponding to the three-dimensional femoral image as P=(θx, θy, θz, Px, Py, Pz), where θx, θy and θz represent rotation angles of a femur around three principal axes, X, Y and Z, in a projection reference coordinate system, respectively; Px, Py and Pz represent translation amounts of the femur in directions of the three principal axes, X, Y and Z, in the projection reference coordinate system, respectively; and a DRR image generating unit, configured to project the three-dimensional femoral image with the surgical path along the three principal axes at intervals of a preset translation length and a preset rotation angle to generate the plurality of DRR images.

The DRR image feature point extraction module 807 specifically includes:

a unit for generating a femoral outer contour and a series of contour circles, configured to perform data processing on the DRR image to generate a femoral outer contour and a series of contour circles of a femoral head of the DRR image; and a DRR image feature point extraction unit, configured to extract intersection points of the series of contour circles and the femoral outer contour as the feature points of the DRR image.

The image registration module 808 specifically includes:

an image registration unit, configured to compare the similarity between the feature points of the X-ray image with the feature points of the DRR image, and if an anteroposterior/posteroanterior image and a lateral image successfully match within an error range, obtain a surgical path of a successfully matched DRR image; and a unit for outputting a surgical path after registration, configured to output the surgical path after registration based on the surgical path of the successfully matched DRR image.

In some embodiments, the image registration system according to the embodiment of the present disclosure has functions or included modules that can be used to perform the image registration method described in the above method embodiment, and for its specific implementation, reference may be made to the description of the above method embodiment, which is not repeated herein for brevity.

According to an embodiment of the present disclosure, the present disclosure further provides an electronic device and a readable storage medium for performing the above method.

Figure 9:
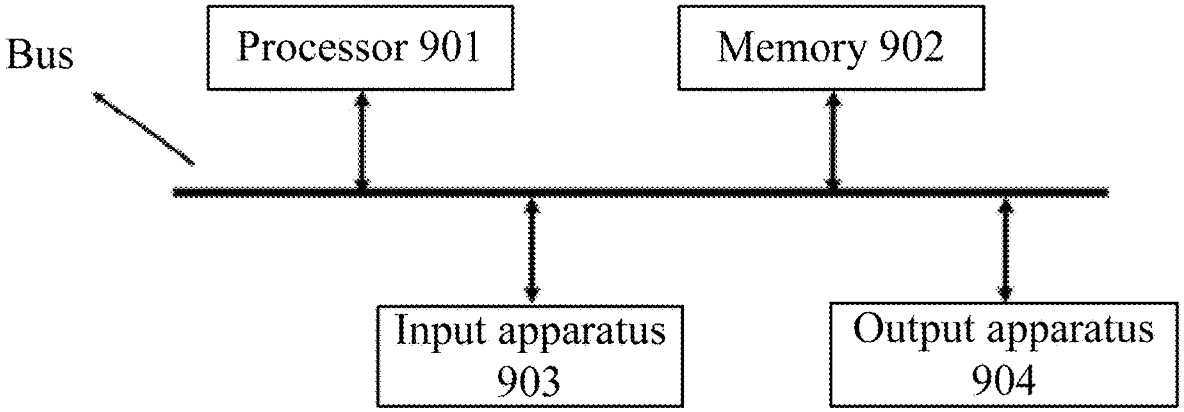
FIG. 9 is a schematic structural diagram of an electronic device and a computer-readable storage medium according to an embodiment of the present disclosure.

FIG. 9 is a schematic diagram of an electronic device and a storage medium for implementing an image registration method for navigation in femoral neck fracture surgery according to an embodiment of the present disclosure. The electronic device includes one or more processors 901, a memory 902, an input apparatus 903, an output apparatus 904, and interfaces for connecting various components, which include a high-speed interface and a low-speed interface. The components are interconnected by using different buses, and can be installed on a common mainboard or installed in other ways as required.

The processor 901 can process instructions executed within the electronic device, including instructions stored in or on a memory to display graphical information of a graphical user interface (GUI) on an external input/output apparatus (such as a display device coupled to an interface). In other implementations, if necessary, a plurality of electronic devices may be connected, and each device provides some necessary operations (for example, as a server array, a group of blade servers, or a processor system).

The processor 901 may be various general-purpose or special-purpose processing assemblies with processing and computing capabilities. Some examples of the processor 901 include, but are not limited to, a central processing unit (CPU), a graphics processing unit (GPU), various dedicated artificial intelligence computing chips, various computing units for running machine learning model algorithms, a digital signal processor (DSP), any appropriate processor, controller and microcontroller, and the like. The processor 901 performs the image registration method for navigation in femoral neck fracture surgery described above.

The memory 902 is a non-transitory computer-readable storage medium according to the present disclosure. The memory 902 stores instructions executable by at least one processor, such that the at least one processor 901 performs the image registration method for navigation in femoral neck fracture surgery according to the present disclosure. The non-transitory computer-readable storage medium according to the present disclosure stores computer instructions, and the computer instructions are used to enable a computer to perform the image registration method for navigation in femoral neck fracture surgery according to the present disclosure.

The memory 902 may include a program storage area and a data storage area, where the program storage area is configured to store an operating system and application programs required for at least one function; and the data storage area can store data created during use of the electronic device for image registration for navigation in femoral neck fracture surgery. Moreover, the memory 902 may further include a high-speed random access memory and a non-transitory memory, such as at least one disk storage device, a flash memory device, or other non-transitory solid-state memory devices.

In some embodiments, the memory 902 may optionally include memories remotely arranged relative to the processor 901, and these remote memories may be connected to the electronic device for image registration for navigation in femoral neck fracture surgery via a network. Embodiments of the above network may be Internet, intranet, a local area network, a mobile communication network, and a combination thereof, but are not limited thereto.

The input apparatus 903 can receive input digital or character instructions, and generate a key signal input related to user settings and function control of the electronic device for image registration for navigation in femoral neck fracture surgery, and is, for example, a touch screen, a keypad, a mouse, a touchpad, a pointing stick, one or more mouse buttons, a trackball, and a joystick.

The output apparatus 904 may include a display device (such as a track pad), a feedback apparatus (such as a vibrating motor), and the like. Some auxiliary devices may be added, including but not limited to, for example, a liquid crystal display (LCD), a light-emitting diode (LED) display, and a plasma display.

In some embodiments, the display device may be a touch screen. In this embodiment, the input apparatus is closely related to the output apparatus.

Embodiments of this description are described in a progressive manner, each embodiment focuses on the difference from other embodiments, and for the same and similar parts between the embodiments, reference may be made to each other. Since the system disclosed in an embodiment corresponds to the method disclosed in an embodiment, the description is relatively simple, and for related contents, reference may be made to the description of the method.

Specific examples are used herein for illustration of principles and implementation modes of the present disclosure. The descriptions of the above embodiments are merely used for assisting in understanding the method of the present disclosure and its core ideas. In addition, those of ordinary skill in the art can make various modifications in terms of specific implementations and the scope of application in accordance with the ideas of the present disclosure. In conclusion, the content of this description shall not be construed as limitations to the present disclosure.

What is claimed is:

1. An image registration method for navigation in femoral neck fracture surgery, comprising:

obtaining femoral image data by a computed tomography (CT) imaging device before femoral neck fracture surgery;

reconstructing and segmenting the femoral image data to generate a three-dimensional femoral image;

obtaining a surgical path planned by a doctor on the three-dimensional femoral image to generate a three-dimensional femoral image with the surgical path;

obtaining, during the femoral neck fracture surgery, X-ray images photographed by an X-ray machine at different angles, wherein the different angles comprise an anteroposterior/posteroanterior view and a lateral view;

performing data processing on each of the X-ray images, and extracting feature points of each of the X-ray images;

setting digitally reconstructured radiograph (DRR) virtual scene projection parameters based on a structure of the X-ray machine, projecting the three-dimensional femoral image with the surgical path to generate a plurality of DRR images, and obtaining projection pose coordinates and a surgical path of each of the DRR images;

performing data processing on the DRR images, and extracting feature points of each of the DRR images; and for each DRR image of the plurality of DRR images, automatically registering the DRR image with each of the X-ray images based on similarities between the feature points of each of the X-ray images and the feature points of the DRR image, and outputting a surgical path after registration.

2. The image registration method according to claim 1, wherein performing data processing on the X-ray images, and extracting the feature points of each of the X-ray images specifically-comprises:

obtaining regional feature points selected in a femoral head region of each of the X-ray images;

generating a femoral head fitting circle with the regional feature points;

generating a series of contour circles based on the femoral head fitting circle;

identifying a femoral outer contour of the X-ray images based on a femoral outer contour line segment template; and extracting intersection points of the series of contour circles and the femoral outer contour as the feature points of each X-ray image.

3. The image registration method according to claim 2, wherein setting the DRR virtual scene projection parameters based on the structure of the X-ray machine, projecting the three-dimensional femoral image with the surgical path to generate the plurality of DRR images comprises:

setting the DRR virtual scene projection parameters based on the structure of the X-ray machine, and expressing a pose parameter corresponding to the three-dimensional femoral image as $P=(\theta x, \theta y, \theta z, Px, Py, Pz)$, wherein $\theta x$, $\theta y$ and $\theta z$ represent rotation angles of a femur around three principal axes, X, Y and Z, in a projection reference coordinate system, respectively; Px, Py and Pz represent translation amounts of the femur in directions of the three principal axes, X, Y and Z, in the projection reference coordinate system, respectively; and projecting the three-dimensional femoral image with the surgical path along the three principal axes at intervals of a preset translation length and a preset rotation angle to generate the plurality of DRR images.

4. The image registration method according to claim 3, wherein performing data processing on the DRR images, and extracting the feature points of each of the DRR images comprises:

performing data processing on each of the DRR images to generate a femoral outer contour and a series of contour circles of a femoral head of each DRR image; and extracting intersection points of the series of contour circles and the femoral outer contour as the feature points of each DRR image.

5. The image registration method according to claim 4, wherein for each DRR image of the plurality of DRR images, automatically registering the DRR image with each of the X-ray images based on between the feature points of each of the X-ray images and the feature points of the DRR image, and outputting the surgical path after registration comprises:

for each DRR image of the plurality of DRR images, comparing the similarities between the feature points of each of the X-ray images with the feature points of the DRR image, and in a case that an anteroposterior/posteroanterior image and a lateral image successfully match within an error range, obtaining a surgical path of a successfully matched DRR image; and outputting the surgical path after registration based on the surgical path of the successfully matched DRR image.

6. An electronic device, comprising one or more processors and one or more memories configured to store one or more programs, wherein when the one or more programs are executed by the one or more processors, the one or more processors are enabled to implement the image registration method for navigation in femoral neck fracture surgery according to claim 1.

7. A computer-readable storage medium, in which computer instructions are stored, wherein when the computer instructions are executed, the computer-readable storage medium is enabled to implement the image registration method for navigation in femoral neck fracture surgery according to claim 1.

8. An image registration system for navigation in femoral neck fracture surgery, comprising:

a femoral image data acquisition module, configured to obtain femoral image data by a CT imaging device before femoral neck fracture surgery;

a three-dimensional femoral image reconstruction module, configured to reconstruct and segment the femoral image data to generate a three-dimensional femoral image;

a surgical path planning module, configured to obtain a surgical path planned by a doctor on the three-dimensional femoral image to generate a three-dimensional femoral image with the surgical path;

an X-ray image acquisition module, configured to obtain, during the femoral neck fracture surgery, X-ray images photographed by an X-ray machine at different angles, wherein the different angles comprise an anteroposterior/posteroanterior view and a lateral view;

an X-ray image feature point extraction module, configured to perform data processing on each of the X-ray images, and extract feature points of each of the X-ray images;

a DRR image generation module, configured to set DRR virtual scene projection parameters based on a structure of the X-ray machine, project the three-dimensional femoral image with the surgical path to generate a plurality of DRR images, and obtain projection pose coordinates and a surgical path of each of the DRR images;

a DRR image feature point extraction module, configured to perform data processing on the DRR images, and extract feature points of each of the DRR images; and an image registration module, configured to for each DRR image of the plurality of DRR images, automatically register the DRR image with each of the X-ray images based on similarities between the feature points of each of the X-ray images and the feature points of the DRR image, and output a surgical path after registration.

9. The system according to claim 8, wherein the X-ray image feature point extraction module comprises:

a regional feature point selection unit, configured to obtain regional feature points selected in a femoral head region of each of the X-ray images;

a femoral head fitting circle generating unit, configured to generate a femoral head fitting circle with the regional feature points;

a unit for generating a series of contour circles, configured to generate a series of contour circles based on the femoral head fitting circle;

a femoral outer contour identification unit, configured to identify a femoral outer contour of the X-ray images based on a femoral outer contour line segment template; and an X-ray image feature point extraction unit, configured to extract intersection points of the series of contour circles and the femoral outer contour as the feature points of each X-ray image.

10. The system according to claim 9, wherein the DRR image generation module comprises:

a DRR virtual scene projection parameter setting unit, configured to set the DRR virtual scene projection parameters based on the structure of the X-ray machine, and express a pose parameter corresponding to the three-dimensional femoral image as P=(θx, θy, θz, Px, Py, Pz), wherein θx, θy and θz represent rotation angles of a femur around three principal axes, X, Y and Z, in a projection reference coordinate system, respectively; Px, Py and Pz represent translation amounts of the femur in directions of the three principal axes, X, Y and Z, in the projection reference coordinate system, respectively; and a DRR image generating unit, configured to project the three-dimensional femoral image with the surgical path along the three principal axes at intervals of a preset translation length and a preset rotation angle to generate the plurality of DRR images.

* * * * *